US007360538B2

(12) United States Patent
Flynn

(10) Patent No.: US 7,360,538 B2
(45) Date of Patent: Apr. 22, 2008

(54) OXYGEN THERAPY FACE MASK

(76) Inventor: Stephen Flynn, 1108 South Service Road West, Oakville (CA) L6L 5T7

( * ) Notice: Subject to any disclaimer, the term of this patent is extended or adjusted under 35 U.S.C. 154(b) by 0 days.

(21) Appl. No.: 11/182,791

(22) Filed: Jul. 18, 2005

(65) Prior Publication Data

US 2007/0012360 A1    Jan. 18, 2007

(51) Int. Cl.
*A61M 16/00*    (2006.01)
(52) U.S. Cl. .................. 128/205.13; 128/205.14; 128/205.15; 128/205.16; 128/205.17; 128/205.24; 128/205.25; 128/204.28; 128/206.15; 128/207.12
(58) Field of Classification Search .......... 128/205.24, 128/205.25, 205.29, 205.27, 206.12, 206.15, 128/206.18, 206.19, 207.12, 206.28, 206.21, 128/204.11, 204.12, 204.13
See application file for complete search history.

(56) References Cited

U.S. PATENT DOCUMENTS

| | | | | | |
|---|---|---|---|---|---|
| 2,166,164 | A | * | 7/1939 | Lehmberg | 128/206.24 |
| 3,097,642 | A | * | 7/1963 | Russell | 128/205.17 |
| 3,726,274 | A | * | 4/1973 | Bird et al. | 128/205.24 |
| 4,077,404 | A | * | 3/1978 | Elam | 128/204.28 |
| 4,098,271 | A | * | 7/1978 | Maddock | 128/202.22 |
| 4,649,912 | A | * | 3/1987 | Collins | 128/202.13 |
| 5,020,530 | A | * | 6/1991 | Miller | 128/203.28 |
| 5,692,498 | A | * | 12/1997 | Lurie et al. | 128/205.24 |
| 6,871,648 | B1 | * | 3/2005 | Winekoff | 128/205.13 |
| 6,883,518 | B2 | * | 4/2005 | Mittelstadt et al. | 128/206.15 |
| 7,007,695 | B2 | * | 3/2006 | Curran et al. | 128/206.15 |
| 2002/0104531 | A1 | * | 8/2002 | Malone | 128/200.23 |

* cited by examiner

*Primary Examiner*—Patricia Bianco
*Assistant Examiner*—Nihir Patel
(74) *Attorney, Agent, or Firm*—Robert F. Delbridge

(57) ABSTRACT

An oxygen therapy face mask has a face engaging portion and a valve assembly connected thereto. The valve assembly has a first passage communicating with the interior of the face engaging portion from which gas can flow into the face engaging portion and into a patient's mouth and nose and which can also receive gas from a patient's mouth and nose and the interior of the face engaging portion. A first one-way valve is associated with the first passage and a second passage connectable to an oxygen reservoir bag and to an external source of pressurized oxygen. The first one-way valve is operable to permit flow of gas from the second passage to the first passage and to prevent flow of gas from the first passage to the second passage. A second one-way valve is associated with the first passage and is operable to permit flow of gas from the first passage to the external atmosphere and to prevent flow of gas from the external atmosphere to the first passage. A third one-way valve is associated with the first passage and is operable to permit flow of gas from the external atmosphere to the first passage and to prevent flow of gas from the first passage to the external atmosphere. A patient can inhale oxygen which passes from the second passage through the first one-way valve and can also inhale air from the external atmosphere through the third one-way valve if sufficient oxygen is not available in the second passage.

5 Claims, 2 Drawing Sheets

OXYGEN THERAPY FACE MASK

FIELD OF INVENTION

This invention relates to oxygen therapy face masks which supply a patient with oxygen from a pressurize source thereof.

BACKGROUND OF INVENTION

There are various medical conditions which require a patient to be supplied with substantially pure oxygen. It is conventional practice to place a mask on the patient's mouth and nose and to supply pressurized oxygen to the mask through a reservoir bag and an appropriate valve assembly. A disadvantage of known masks of this kind is that the patient's demand for oxygen may be greater than the supply with the result that medical personnel or the patient have to tamper with the mask so that the patient also receives air from the external atmosphere.

It is an object of the present invention to provide a face mask which substantially overcomes the problem mentioned above.

SUMMARY OF INVENTION

According to the present invention, an oxygen therapy face mask has a face engaging portion and a valve assembly connected thereto, said valve assembly having a first passage communicating with the interior of the face engaging portion from which gas can flow into the face engaging portion and into a patient's mouth and nose and which can also receive gas from a patient's mouth and nose and the interior of the face engaging portion. A first one-way valve associated with the first passage and a second passage connectable to an oxygen reservoir bag and to an external source of pressurized oxygen, said first one-way valve being operable to permit flow of gas from the second passage to the first passage and to prevent flow of gas from the first passage to the second passage. A second one-way valve associated with the first passage and operable to permit flow of gas from the firs passage to the external atmosphere and to prevent flow of gas from the external atmosphere to the first passage. A third one-way valve associated with the first passage and operable to permit flow of gas from the external atmosphere to the first passage and to prevent flow of gas from the first passage to the external atmosphere. A patient can inhale oxygen which passes from the second passage through the first one-way valve and can also inhale air from the external atmosphere through the third one-way valve if sufficient oxygen is not available in the second passage.

The valve assembly may also have a filter to filter gas passing from the first passage through the second one-way valve to the external atmosphere.

The first one-way valve may comprise a disk-like diaphragm located between the first and second passages and one of the other one-way valves may comprise an annular diaphragm surrounding the disk-like diaphragm of the first one-way valve.

The face engaging portion may have a readily openable and closeable aperture to enable medication to be directly passed into the interior of the face engaging portion from a pressurized pre-measured dose medication container.

DESCRIPTION OF THE DRAWINGS

One embodiment of the invention will now be described, by way of example, with reference to the accompanying drawings, of which.

DESCRIPTION OF PREFERRED EMBODIMENT

Figure 1:
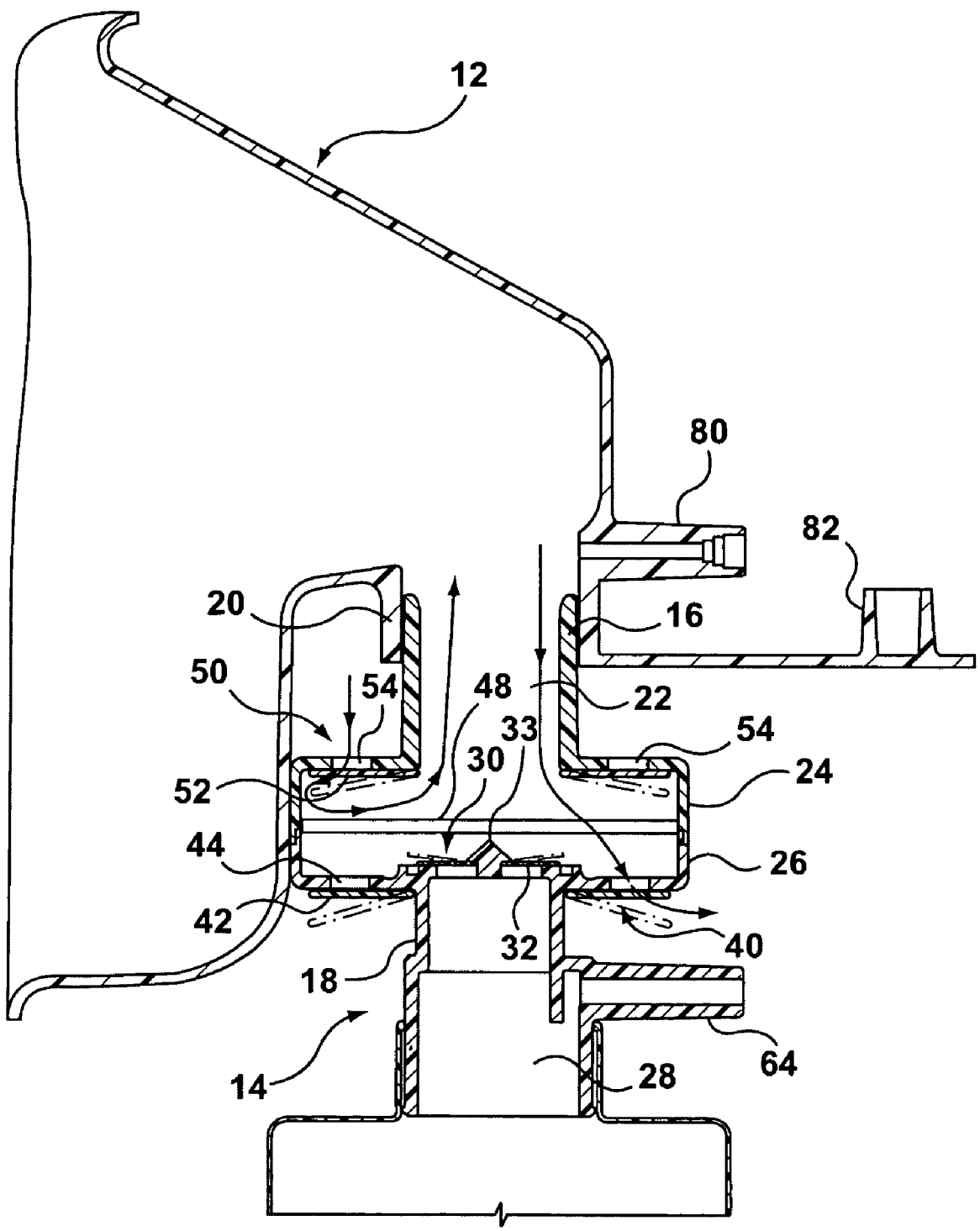
FIG. 1 is a sectional view of an oxygen therapy face mask.

Referring to the drawings, an oxygen therapy face mask has a face engaging portion 12 of soft flexible transparent plastic material and a valve assembly 14 connected thereto. The valve assembly 14 has an upper tubular body portion 16 and a lower tubular body portion 18 connected thereto. The upper tubular body portion 16 has its upper end portion inserted into a downwardly extending tubular portion 20 of the face engaging portion 12.

The upper tubular body portion 16 provides a first passage 22. The lower end portion 24 of the upper tubular body portion 16 is enlarged, as also is the upper end portion 26 of the lower tubular body portion 18. The enlarged upper end portion 26 of the lower tubular body portion 18 is secured to the enlarged lower end portion 24 of the upper tubular body portion 16. The lower tubular body portion 18 provides a second passage 28.

A first one-way valve 30 is provided at the junction of the first and second passages 22, 28. The first one-way valve 30 comprises a disk-like diaphragm 32 at the upper end of the second passage 28. The disk-like diaphragm 32 is retained in position by a central headed pin 33 carried by the lower tubular body portion 18. Normally, the diaphragm 32 closes the upper end of the second passage 28, but a sufficiently higher pressure in the second passage 28 relative to the pressure in the first passage 22 causes the diaphragm 32 to move upwardly and permit gas to flow from the second passage 28 into the first passage 22.

A second one-way valve 40 comprises an annular diaphragm 42 which surrounds the disk-like diaphragm 32 of the first one-way valve 30. The annular diaphragm 42 normally closes apertures 44 in the lower part of the enlarged upper portion 26 of the lower tubular body portion 18. A filter 48 extends across the lower end portion of the first passage 22 at the junction of the enlarged lower end portion 24 of the upper tubular portion 16 and the enlarged upper end portion 26 of the lower tubular body portion 18.

A third one-way valve 50 comprises an annular diaphragm 52 at the top of the enlarged lower end portion 26 of the upper tubular body portion 16. The annular diaphragm 52 normally closes apertures 54 in the enlarged lower end portion 24 of the upper tubular body portion 16 to isolate the first passage way 22 from the external atmosphere. The construction of the first and third one-way valves 30, 50 is such that the third one-way valve 50 normally remains closed when oxygen is being inhaled by a patient after passage through the first one-way valve 30.

The face engaging portion 12 has a tubular inlet 80 through which medication can be directly passed into the interior of the face engaging portion 12 of the mask from a pressurized pre-measured dose medication container (not shown). The inlet 80 is near the patient's mouth and nose and hence provides a very efficient means for supplying medication to the patient. The tubular inlet 80 is normally closed by a closure 82.

Figure 2:
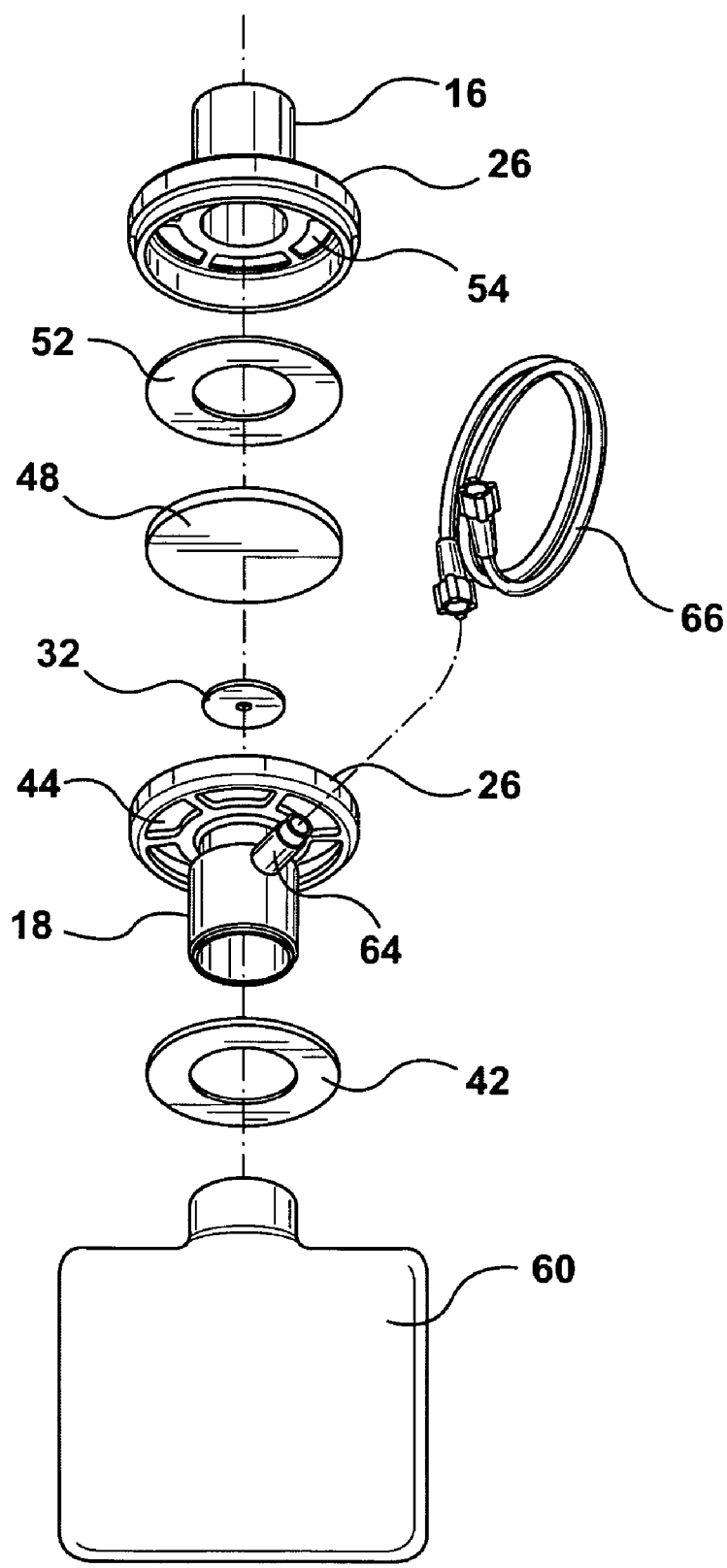
FIG. 2 is an exploded view of the valve assembly of FIG. 1.

As indicated in FIG. 2, a gas reservoir bag 60 is mounted on the lower end of lower tubular body portion 18. The lower tubular body portion 18 has a tubular inlet 64 which is connectable by a flexible tube 66 to a source of pressurized oxygen (not shown).

When the face engaging portion 12 has been placed over the patient's mouth and nose, with the oxygen reservoir bag 60 in place and the oxygen inlet 64 connected to a source of pressurized oxygen, with the medication inlet 80 being closed, inhaling by the patient will cause the first one-way valve 30 to open so that oxygen passes through the second passage 28 to the first passage 22 and through the filter 48 into the the face engaging portion 12 and into the patient's mouth and nose. The pressure of the oxygen in the second passage 28 assists with the opening of the first one-way valve 30 when the patient inhales (with consequent lowering of pressure in the first passage 22). The lower pressure in the first passage 22 causes the second one-way valve 40 to remain closed. The third one-way valve 50 remains closed because the lower pressure in the first passage 22 is not sufficiently low to cause it to open.

When the patient exhales, the increase in pressure in the first passage 22 causes the first one-way valve 30 to close and the third one-way valve 50 to remain closed. The increase in pressure in the first passage 22 then causes the second one-way valve 40 to open so that air in the first passage 22 passes therethrough and through the filter 48 to the external atmosphere.

Such inhaling and exhaling continues while the oxygen supply to the second passage 28 is sufficient, with the reservoir bag 60 functioning in the conventional manner. If the oxygen supply ceases, so that there is little or no oxygen flow through the first one-way valve 30, further lowering of pressure in the first passage 22 produced by the patient inhaling more strongly causes the third one-way valve 50 to open. Air is then drawn through the third one-way valve 50 from the external atmosphere into the first passage 22 and hence to the patient.

Thus, neither the patient nor medical personnel need to tamper with the face mask if the oxygen supply fails, and the patient continues to exhale through the filter 48. The advantages of the invention will now be readily apparent to a person skilled in the art from the foregoing description of a preferred embodiment. Other advantages and embodiments will also now be readily apparent, the scope of the invention being defined in the appended claims.

The invention claimed is:

1. An oxygen therapy face mask having:
   a face engaging portion and a valve assembly connected thereto;
   said valve assembly having a first passage communicating with the interior of the face engaging portion from which gas can flow into the face engaging portion and into a patient's mouth and nose and which can also receive gas from a patient's mouth and nose and the interior of the face engaging portion;
   a first one-way valve associated with the first passage and a second passage connectable to an oxygen reservoir bag and to an external source of pressurized oxygen, said first one-way valve being operable to permit flow of gas from the second passage to the first passage and to prevent flow of gas from the first passage to the second passage;
   a second one-way valve associated with the first passage and operable to permit flow of gas from the first passage to the external atmosphere and to prevent flow of gas from the external atmosphere to the first passage; and
   a third one-way valve associated with the first passage and operable to permit flow of gas from the external atmosphere to the first passage and to prevent flow of gas from the first passage to the external atmosphere;
   the first one-way valve comprising a disk-like diaphragm located between the first and second passages and movable between open and closed positions and one of the other one-way valves comprises an annular diaphragm surrounding the disk-like diaphragm of the first one-way valve and movable between open and closed positions;
   whereby a patient can inhale oxygen which passes from the second passage through the first one-way valve and can also inhale air from the external atmosphere through the third one-way valve if sufficient oxygen is not available in the second passage.

2. A face mask according to claim 1 wherein the valve assembly also has a filter to filter gas passing from the first passage through the second one-way valve to the external atmosphere.

3. A face mask according to claim 1 wherein the face engaging portion has a readily openable and closeable aperture to enable medication to be directly passed into the interior of the face engaging portion from a pressurized pre-measured dose medication container.

4. A valve assembly for an oxygen therapy face mask, said valve assembly having a first passage connectable to the interior of a face engaging portion of the face mask from which gas can flow into the face engaging portion and into a patient's mouth and nose and which can also receive gas from the patient's mouth and nose and the interior of the face engaging portion;
   a first one-way valve associated with the first passage and second passage connectable to an oxygen reservoir bag and to an external source of pressurized oxygen, said first one-way valve being operable to prevent flow of gas from the second passage to the first passage and prevent flow of gas from the first passage to the second passage;
   a second one-way valve associated with the first passage and operable to prevent flow of gas from the first passage to the external atmosphere and to prevent flow of gas from the external atmosphere to the first passage; and
   a third one-way valve associated with the first passage and operable to permit flow of gas from the external atmosphere to the first passage and to prevent flow of gas from the first passage to the external atmosphere,
   the first one-way valve comprising a disk-like diaphragm located between the first and second passages and movable between open and closed positions and one of the other one-way valves comprising an annular diaphragm surrounding the disk-like diaphragm of the first one-way valve and movable between open and closed positions.

5. A valve assembly according to claim 4 also having a filter to filter gas passing from the first passage through the second one-way valve to the external atmosphere.

* * * * *